United States Patent
Cox et al.

(10) Patent No.: US 6,496,717 B2
(45) Date of Patent: Dec. 17, 2002

(54) RADIO GUIDED SEED LOCALIZATION OF IMAGED LESIONS

(75) Inventors: Charles E. Cox, Tampa, FL (US); Emilia L. Dauway, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 09/413,293

(22) Filed: Oct. 6, 1999

(65) Prior Publication Data

US 2002/0087078 A1 Jul. 4, 2002

Related U.S. Application Data

(60) Provisional application No. 60/103,169, filed on Oct. 6, 1998.

(51) Int. Cl.[7] .................................................. A61B 6/00
(52) U.S. Cl. ........................................... 600/436; 600/8
(58) Field of Search ............................... 600/436, 1, 2, 600/3, 4, 5, 6, 7, 8, 439, 431, 411, 427, 407; 424/111, 9.1

(56) References Cited

U.S. PATENT DOCUMENTS

| | | |
|---|---|---|
| 3,936,646 A | 2/1976 | Jonker |
| 4,106,488 A | 8/1978 | Gordon |
| 4,763,671 A | 8/1988 | Goffinet |
| 4,959,547 A | 9/1990 | Carroll et al. |
| 5,030,195 A * | 7/1991 | Nardi ............................ 600/7 |
| 5,119,818 A | 6/1992 | Carroll et al. |
| 5,141,487 A | 8/1992 | Liprie |
| 5,170,055 A | 12/1992 | Carroll et al. |
| 5,282,781 A | 2/1994 | Liprie |
| 5,308,604 A * | 5/1994 | Sinn et al. .................. 424/1.53 |
| 5,342,283 A * | 8/1994 | Good .......................... 376/158 |
| 5,441,050 A | 8/1995 | Thurston et al. |
| 5,482,040 A | 1/1996 | Martin, Jr. |
| 5,624,372 A | 4/1997 | Liprie |
| 5,635,717 A | 6/1997 | Popescu |
| 5,694,933 A | 12/1997 | Madden et al. |
| 5,716,595 A | 2/1998 | Goldenberg |
| 5,732,704 A | 3/1998 | Thurston et al. |
| 5,813,985 A | 9/1998 | Carroll |
| 5,814,295 A | 9/1998 | Martin, Jr. et al. |
| 5,836,882 A | 11/1998 | Frazin |
| 5,846,513 A | 12/1998 | Carroll et al. |
| 5,961,527 A | 10/1999 | Whitmore, III et al. |
| 6,015,390 A | 1/2000 | Krag |
| 6,019,718 A | 2/2000 | Hektner |
| 6,060,036 A | 5/2000 | Armini |
| 6,080,099 A | 6/2000 | Slater et al. |
| 6,083,167 A | 7/2000 | Fox et al. |
| 6,095,975 A | 8/2000 | Silvern |
| 6,102,844 A * | 8/2000 | Ravins et al. .................. 600/8 |
| 6,103,295 A | 8/2000 | Chan et al. |
| 6,135,955 A | 10/2000 | Madden et al. |
| 6,175,760 B1 * | 1/2001 | Baskin et al. ................ 600/431 |
| 6,200,258 B1 * | 3/2001 | Slater et al. .................... 600/8 |
| 6,280,450 B1 * | 8/2001 | McGuckin, Jr. ............. 606/114 |
| 6,311,084 B1 * | 10/2001 | Cormack et al. ........... 600/411 |
| 6,356,782 B1 * | 3/2002 | Sirimanne et al. .......... 128/899 |

* cited by examiner

*Primary Examiner*—Marvin M. Lateef
*Assistant Examiner*—Eleni Mantis Mercader
(74) *Attorney, Agent, or Firm*—Kohn & Associates, PLLC

(57) ABSTRACT

A method of removing lesions by implanting a radioactive seed at the location of the lesion, locating the lesion with the radioactive seed, and removing the lesion with the radioactive seed.

19 Claims, No Drawings

RADIO GUIDED SEED LOCALIZATION OF IMAGED LESIONS

CROSS REFERENCE TO RELATED APPLICATIONS

This application is a conversion of a U.S. Provisional Application Serial No. 60/103,169, filed Oct. 6, 1998, incorporated herein by reference.

BACKGROUND OF THE INVENTION

1. Technical Field

The present invention relates to methods of localizing lesions. More specifically, the present invention relates to methods of localizing lesions using radioactive seeds.

2. Background Art

Localization of non-palpable lesions for biopsy or excision during surgery is a necessary procedure. Several techniques are currently available. As described herein, these techniques have several disadvantages and improved methods are needed.

Mammography is credited with the detection of clinically occult cancer of the breast at greater than 80% sensitivity. Since breast biopsies increase the overall cost of screening for breast cancer and 70% of the detected lesions are benign, there is controversy regarding the cost effectiveness of such biopsies. Therefore, the development of more effective biopsy techniques are a significant goal.

There are three different ways to biopsy occult breast lesions. These include "core-needle" biopsy, "ABBI" (Advanced Breast Biopsy Instrumentation), and open surgical excision biopsy. Open surgical excision biopsy, using needle localization, has been the standard for diagnosis of non-palpable lesions in the breast for the past 20 years.

Although needle localized breast biopsy (NLBB) has some advantages, it has several disadvantages. It requires highest-level skill in placement by radiologists. The method requires flexible wires which are difficult for surgeons to palpate. Currently used wires may be dislodged during transfer of the patient, or displaced from the site of the radiographically located suspicious lesion. When cut inadvertently with scissors, the wires may leave metal fragments in the patient's breast, which has resulted in litigation. A potential for thermal injury to the breast exists when electrocautery is used near the wire. If the insertion site of the wire is too far from the lesion, there is a dilemma in planning the incision to include both the wire and the lesion. This situation can lead to removing more breast tissue than necessary. There are increased costs related to additional x-rays which are used to confirm that the lesion has been excised, longer operating room time fees, specimens require transfer to radiology by operating room personnel, taking a film of the specimen by a radiology technician and finally interpretation and notification by a radiologist.

Recently, several patents have issued pertaining to devices and methods for the removal of lesions from soft tissue. However, these patients do little to overcome the problems detailed above. Specifically, U.S. Pat. No. 5,807,276 to Russin, issued September 1998, discloses a device and method for using a K-wire which is positioned through the lesion to be removed. This device requires that selectable wires be used which can be difficult to maneuver and may cause infection if not properly sterilized.

U.S. Pat. No. 5,833,627 to Shmulewitz et al., issued November 1998, also discloses a needle or cannula of a biopsy device for insertion into the tissue. This is accomplished by correlating, in real-time, the actual needle or cannula position with its probable trajectory once inserted. There is a large amount of speculation involved in the insertion of the needle into the breast or other soft tissue, thus increasing the possibility of removing more soft tissue than is necessary.

Finally, U.S. Pat. No. 5,855,554 to Schneider et al., issued January 1999, discloses support plates which contain the breast. The plates include grids with reference markers for localization and windows for allowing the physician access to the breast. A thick biopsy plate containing a plurality of holes fits into the grid opening through which the biopsy needle is inserted. Again, the same problems pertaining to the insertion of wires or needles can occur which can lead to the removal of excess breast tissue.

Although the above discussed biopsies are done for the diagnosis of cancer, it is imperative that physicians treat the lesions as if they are malignant until it is histologically proven otherwise. Lesions should be removed by the most direct approach, as opposed to tracking the lesion and needle through breast tissue. The surgeon also needs to be aware of the placement of the incision so that if a mastectomy is necessary in the future, the biopsy scar can be cleanly excised.

It is therefore desirable to develop a method whereby mammographically detected lesions can be localized and excised in a safe, expeditious, and cost effective manner with the application of current technologies.

SUMMARY OF THE INVENTION

According to the present invention, there is provided a method of removing lesions by implanting a radioactive seed at the location of the lesion, locating the lesion for surgery by detecting the radioactivity of the implanted radioactive seed, and removing the lesion with the radioactive seed.

DETAILED DESCRIPTION OF THE INVENTION

The present invention provides a method of removing lesions from soft tissues or bone by implanting a radioactive seed at the location of the lesion, locating the lesion by detecting radioactivity from the radioactive seed and then removing the lesion along with the radioactive seed.

The present method utilizes radiographic imaging or x-ray techniques such as CT scan, PET scan, MRI, or mammography to ensure that the radioactive seed is implanted in the exact location of the lesion, thus eliminating unnecessary removal of soft tissue, such as breast tissue, during the biopsy.

As further defined and explained below, the term "implanted" means placing by needle placement, needle localization, surgery, injection or otherwise, the radioactive seed proximate to or within the lesion. This provides a precise target for the surgeon based upon a reliable identification of the lesion by radiographic imaging. By radioactive seed, it is meant that a radioactive, inert pellet is utilized. Such pellets can be made from an implantable metal, such as titanium, and the pellet also contains a radioisotope. The radioimmission can be gamma radiation or other emissions which are benign to the lesion and tissue and can just be detected by known detecting devices and methods. An example of such a radioactive seed is disclosed in U.S. Pat. No. 5,460,592 to Langton et al., assigned to Amersham.

In the past, radioactive seeds have been used for temporary as well as permanent implantation. The recaptured seeds can be sterilized for reuse. The most popular use for therapeutic seeds have been in the treatment of meningiomas and prostate cancer. At the Moffitt Cancer Center, improved seed placement technique has been developed for prostate brachytherapy, which has significantly contributed to the decreased morbidity and increased efficacy of the procedure.

The use of low dose seeds, which are temporarily placed, are useful for diagnostic purposes by guiding the biopsy of the suspicious lesion with the assistance of a hand-held gamma detecting probe (Navigator, USSC, Neoprobe, Dublin) or other radiation detecting device, such as a beta radiation detecting device. The present invention utilizes a single 125-I seed of the lowest possible activity (<0.30 mci). This amount of radioactivity is significantly less than a standard mammogram or chest x-ray, however can be detected by the hand-held gamma probe to guide the surgeon in the biopsy process.

These probes have been especially designed to assist in detecting radioactive materials used for diagnostic purposes during surgery. Examples of these procedures include radio-immunoguided surgery (RIGS) for the detection of colorectal tumors and sentinel lymph node mapping for melanoma and breast cancer. Sentinel lymph node mapping, a procedure well known to the Moffit Cancer Center, involves injecting filtered technetium-99 labeled sulfur colloid (450 uci/5 cc) at the primary tumor site and allowing time for this substance to infuse the lymphatic channels. The seed guided breast biopsy utilize radioactive material which would be contained in titanium and have no direct contact with the tissue.

More specifically, the present invention provides a method of localization using the radioactive seeds and hand-held gamma detectors for surgery. The radioactive seed is localized to a lesion by use of imaging technology. The surgeon can then determine the location of the seed during surgery using a hand-held gamma detector. This allows localization without guide wires, a potential source of infection. Further it reduces the number and location of incisions that must be made and which must be considered in future surgeries.

The radioactive seed can be placed and localized to at least the bone, brain, lung, GI tract, intestines, stomach, liver, kidneys, GU tract including prostate, soft tissues, fatty lesions or muscle, pancreas, adrenal or any other site that can be radiographically images or otherwise localized.

Localization can be done with standard radiographs such as mammograms, ultrasound, MRI, CT scan or any other scanning technology that can localize an otherwise non-visible or non-palpable lesion.

In one example of the method, radioactive-guided breast biopsy is utilized. It is a safe, expeditious and cost-effective technique to biopsy non-palpable breast lesions. Low dose radioactive seeds are disposed proximate to a lesion under radiographic guidelines. The seeds are localize the non-palpable breast lesion which allows them to be more effectively excised with reduced operative time.

In a further example of the use of the present invention, interstitial brachytherapy is used. Interstitial brachytherapy has had many applications in the treatment of various malignant neoplasms. The development of accurate placement of radioactive seeds has eliminated many of the problems related to interstitial brachytherapy from past years. A variety of seeds have been developed to take advantage of their individual characteristics. The most widely used radioactive seed for prostate brachytherapy incorporates I-125, however any seed can be used which is detectable by a radiation sensing device. The iodine source is encapsulated in a titanium shell. The titanium combines low radiation absorption with good strength and tissue tolerance. I-125 has a half-life of 60 days and a gamma radiation of only 27 kev. The seeds are available at a length of 4.5 mm and diameter of 0.8 mm, which passes easily through a standard 18-gauge needle.

The above discussion provides a factual basis for the use of radio guided seed localization of imaged lesions. The utility of the present invention is shown by the following non-limiting examples.

EXAMPLE 1

Mammographic placement of a single 125-I seed by the radiologist is performed. Once the patient is placed in the mammographic device and the location of the lesion is determined, the skin is cleansed. Local anesthetic is injected at the site of the placement. An 18-gauge needle with sterile bone wax occluding the tip is loaded with a single 125-I seed. The needle is placed into the breast tissue under mammographic guidance to the suspicious lesion. A stilette is placed into the bore of the needle displacing the seed through the tip. The needle and stilette apparatus are removed from the breast tissue. The seed location is confirmed to be at the lesion with mammography and films are taken. The patient is then taken to the operating room.

The patient is prepared and draped in the normal sterile fashion. A sterile sleeve is placed over a Neoprobe™ gamma counter. The hand-held probe is then run across the skin surface of the breast, marking the exact point of highest count. This clearly identifies the location of the seed and lesion. This area is then anesthetized with local anesthetic. A number 15 blade scalpel is used to make the skin incision. The lesion is removed with the seed in place together with a small margin of surrounding breast tissue. The probe is placed on the specimen and an ex vivo count is taken of the specimen, confirming that the seed has been removed.

The specimen is taken to the specimen processing room. The lesion in the specimen is localized using the gamma detection probe. The specimen is linked using a red color at the hot spot and black for the remaining margins. The specimen is sectioned across the red spot and the seed is removed, placed in a lead container and sent to Radiation Oncology Department for storage. Cytology is made from the lesion for diagnosis. The specimen is fixed in formalin and processed in a routine manner.

By utilizing the present invention, the radiologist need not consider the angle of the placement of the wire and therefore the surgeon has the choice of making the incision directly over the lesion. Therefore, there is less tunneling through the breast and less breast tissue need be removed during the biopsy. Additionally, there is a higher likelihood of immediate localization of the lesion by the surgeon since the use of mammography on site is being provided. There is also a lower possibility of missing a lesion since a hand-held probe can be used to confirm removal of the lesion and the radioactive seed.

Further, the seeds are reusable. This eliminates expense and time required for x-ray imaging of the specimen. Less operating room time is required based on not having to waiting for x-ray confirmation of removal of the lesion. Finally, there is no chance of wire dislodgment, cutting of wire, or retained fragments of wire in the breast tissue which therefore lowers the infection rate since wires are not at all utilized in the present invention.

EXAMPLE 2

Needle localized breast biopsy (NLBBx) has been the standard for diagnosis of nonpalpable lesions for the past 20 years. Low dose radioactive seed localization (RSL) can be used in conjunction with a hand held gamma detector (HHGD) to localize nonpalpable breast lesions and accurately remove the radiographic lesion with reduced operative time (OT) and tissue volume (TV).

Methods

A titanium seed containing 0.05–0.1 mCi of I125 is placed with mammographic or ultrasound guidance localizing the suspicious breast lesion. The HHGD is used to externally locate the seed. The incision is placed directly over the seed/lesion. The HHGD directs the excision and verifies seed/lesion removal. A specimen radiograph (S-Xray) was performed to confirm the seed/lesion removal. Variables included OT, TV, surgeon retrieval success (SRS), and pathologist retrieval success (PRS). Success of identification of the seed/lesion by the surgeon and pathologist were assessed prior to S-Xray utilizing the HHGD.

Results

Fifteen patients underwent successful RSL of nonpalpable breast lesions. OT, TV of RSL and TV of 15 randomly reviewed NLBBx's, SRS and PRS were calculated. The RSL-TV was statistically smaller than the NLBBx-TV (P<0.001).

| RSL-OT (Avg. min) | RSL-TV (Avg. cm3) | NLBBx-TV (Avg. cm3) | SRS (%) | PRS (%) |
|---|---|---|---|---|
| 4.60 + 0.49 | 19.3 + 3.9 | 40.3 + 12.2 | 100 | 100 |

Conclusions

RSL is a safe, time efficient, tissue-sparing method of breast biopsy for image detected lesions. It provides rapid reliable localization by radiologist, surgeon and pathologist possibly eliminating S-Xrays, same day localization, poor wire placement and infection potential of external wires.

EXAMPLE 3

Materials and Methods

Patients were recruited from the Comprehensive Breast Center who had been referred for suspicious mammographically detected lesions requiring NLBB. Variables analyzed included the size and weight of the specimen, total time in the operating room, surgeon retrieval success, and cumulative radiation exposure to the surgeon, radiologist and pathologist.

The technique involves placing a titanium seed containing 0.05–0.1 mCi of I-125 into an 18-gauge needle with sterile bone wax occluding the tip. The apparatus is placed into the breast parenchyma under radiographic guidance (mammography or ultrasound). A stilette is placed into the needle displacing the seed through the tip localizing the lesion. The seed localization is confirmed to be at the lesion with mammography.

After surgical preparation, the sterile sheathed HHGD is utilized to identify location of the seed/lesion by counts of radioactivity. After administration of a local anesthetic, the specimen is removed using the HHGD to guide the depth of dissection. The HHGD is placed on the specimen and an ex-vivo count is taken of the specimen confirming that the seed has been removed. (Initially for the purpose of this study, an x-ray of the specimen was taken to prove that the ex-vivo count was an acceptable replacement for the specimen x-ray.) The pathologist also uses the HHGD to identify and remove the seed from the specimen. The specimen is processed in a routine manner.

Results

Fifteen patients underwent successful removal of RSL of nonpalpable breast lesions. The operative time from incision to specimen removal was 4.60+0.49 min, which ranged from 1 to 8 minutes. Tissue volume of the RSL biopsy specimens were compared to 15 randomly selected NLBB specimens. The RSL specimens average tissue volume was 19.3 cm3+3.9 compared to 40.3 cm3+12.2 for NLBB specimens (p<0.001).

The surgeon was able to retrieve the seed and the lesion and the pathologist able to find the seed in the specimen 100% of the time. The specimen x-ray confirmed retrieval of the lesion in all cases. Definitive on table verification of seed removal by the HHGD occurred likewise 100% of the time. The radiation exposure to the patient, radiologist, surgeon, pathologist and ancillary staff is documented to be minimal by the use of radiation badges and rings worn throughout the procedure.

Conclusion

In summary, the goal was to devise a method whereby mammographically detected lesions can be localized and excised in a safe, expeditious and cost effective manner with application of current technologies. RSL biopsy is a technically feasible procedure requiring minimal radiation exposure and can be performed in an outpatient setting using local anesthetics. RSL and the use of HHGD allow for accurate placement of the incision and precise depth of dissection resulting in less tissue loss. Finally, with enhanced mammographic placement, reduction in operative time and potential replacement of the specimen mammogram, should result in significant cost reduction. The use of low dose diagnostic seeds can be applied to lesions in other organs such as bone, brain, liver, lung, colon, adrenal, kidney, and prostate.

Throughout this application, various publications and patents, are referenced with patents by number and other publications by author and year. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

REFERENCES

U.S. Pat. No. 5,807,276, to Russin.
U.S. Pat. No. 5,833,627, to Schmulewitz et al.
U.S. Pat. No. 5,855,554, to Schneider et al.
U.S. Pat. No. 5,460,592, to Langton et al.
Jackman R J, Marzoni F A Jr. Needle Localized Breast Biopsy: Why Do We Fail? Radiology. 204 (3):677–84, September, 1997

Kopans D B: Breast Imaging, Second Edition. Lippincott-Raven. pp 637–720.

della Rovere G Q, Benson J R, Morgan M, et al: Localization of Impalpable Breast Lesions, A Surgical Approach. European Journal of Surgical Oncology. 22(5):478–82, October, 1996

Khatri V P, Smith D H. Method of Avoiding Tunneling During Needle-Localized Breast Biopsy. J of Surg Onc. 60(1):72–73, September, 1995.

What is claimed is:

1. A method of locating lesions by:

localizing a radioactive seed to a lesion by use of imaging;

locating the lesion by detecting the radioactivity of the radioactive seed having activity of less than or equal to 0.3 mci; and removing the lesion with the radioactive seed.

2. The method according to claim 1, wherein said localizing step further includes the step of implanting the radioactive seed having activity of less than or equal to 0.3 mci at the location of the lesion using radiographic imaging.

3. The method of claim 2, wherein said localizing step further includes the step of verifying proper placement of the radioactive seed.

4. The method according to claim 3, wherein said implanting step further includes locating the lesion using a radiographic image and injecting the radioactive seed at the location found by the radiographic image.

5. The method according to claim 4, wherein said verifying step further includes confirming with an additional radiographic image that the radioactive seed is located at the location of the lesion.

6. The method according to claim 1, wherein said locating step further includes the step of running a radiation detector across the skin surface to determine the highest radiation count.

7. The method according to claim 1, wherein said removing step further includes anesthetizing the area containing the radioactive seed and lesion, surgically removing the lesion, the radioactive seed and a small amount of surrounding tissue; and then verifying that the radioactive seed has been removed.

8. The method according to claim 7, wherein said verifying step further includes placing the radiation detector on the lesion, radioactive seed and the surrounding tissue to take an ex vivo radiation count.

9. The method according to claim 1, wherein said radioactive seed has an activity of less then or equal to 0.12 mci.

10. A method of marking tissue to be studied by:

using a scanning device to locate the tissue;

marking the tissue by placing a radioactive seed having activity of less than or equal to 0.3 mci at the location of the tissue to be studied:

locating the tissue to be studied by detecting the radioactivity of the radioactive seed; and removing the tissue to be studied with the radioactive seed.

11. The method according to claim 10, wherein said marking step further includes the steps of placing the radioactive seed at the location of the tissue using radiographic imaging and verifying proper placement of the radioactive seed.

12. The method according to claim 11, wherein said placing step further includes locating the tissue using a radiographic image and injecting the radioactive seed at the location found by the radiographic image.

13. The method according to claim 11, wherein said verifying step further includes confirming with an additional radiographic image that the radioactive seed is located at the location of the lesion.

14. The method according to claim 10, wherein said using step includes using a scanning device to locate the tissue which is in suspect soft tissue.

15. The method according to claim 10, wherein said marking step includes marking the tissue by placing a radioactive seed which has radioactivity less then or equal to 0.12 mci.

16. The method according to claim 10, wherein said locating step further includes the step of running a radiation detector across the skin surface to determine the highest radiation count.

17. The method according to claim 10, wherein said removing step further includes anesthetizing the area containing the radioactive seed and lesion, surgically removing the lesion, the radioactive seed and a small amount of surrounding tissue; and then verifying that the radioactive seed has been removed.

18. The method according to claim 17, wherein said verifying step further includes placing the radiation detector on the lesion, radioactive seed and the surrounding tissue to take an ex vivo radiation count.

19. The method according to claim 10, wherein said implanting step does not include radiating the tissue to be studied.

\* \* \* \* \*